United States Patent [19]
Paret

[11] Patent Number: 5,123,420
[45] Date of Patent: Jun. 23, 1992

[54] METHOD AND APPARATUS FOR PROCESSING HEART RATE TRACES IN A FETAL MONITOR

[75] Inventor: Guenter Paret, Herrenberg, Fed. Rep. of Germany

[73] Assignee: Hewlett-Packard Company, Palo Alto, Calif.

[21] Appl. No.: 676,853

[22] Filed: Mar. 25, 1991

[51] Int. Cl.$^5$ .............................................. A61B 5/04
[52] U.S. Cl. ................................. 128/698; 128/700; 128/696
[58] Field of Search ............... 128/695, 696, 698, 700, 128/701, 661.07, 662.04, 661.09, 662.01

[56] References Cited

U.S. PATENT DOCUMENTS

| | | | |
|---|---|---|---|
| 3,827,428 | 8/1974 | Hon et al. | 128/2.06 E |
| 4,038,536 | 7/1977 | Feintuch | 128/698 |
| 4,519,396 | 5/1985 | Epstein et al. | 128/698 |
| 4,537,200 | 8/1985 | Widrow | 128/696 |
| 4,569,356 | 2/1986 | Kyozuka | 128/698 |
| 4,751,931 | 6/1988 | Briller et al. | 128/696 |
| 4,781,200 | 11/1988 | Baker | 128/696 |
| 4,793,361 | 12/1988 | DuFault | 128/696 |
| 4,898,179 | 2/1990 | Sirota | 128/698 |

*Primary Examiner*—Francis Jaworski
*Assistant Examiner*—George Manuel

[57] ABSTRACT

A fetal monitor capable of recording the heart rate trace, preferably the beat-to-beat heart rate trace, of a fetus and a second heart rate trace of the mother or of a second fetus. Coincidence between the heart rate traces is detected by means of a direct or indirect comparison of the two traces and comparison of the difference with a predefined or adaptive limit. A warning signal is generated if coincidence is detected.

47 Claims, 7 Drawing Sheets

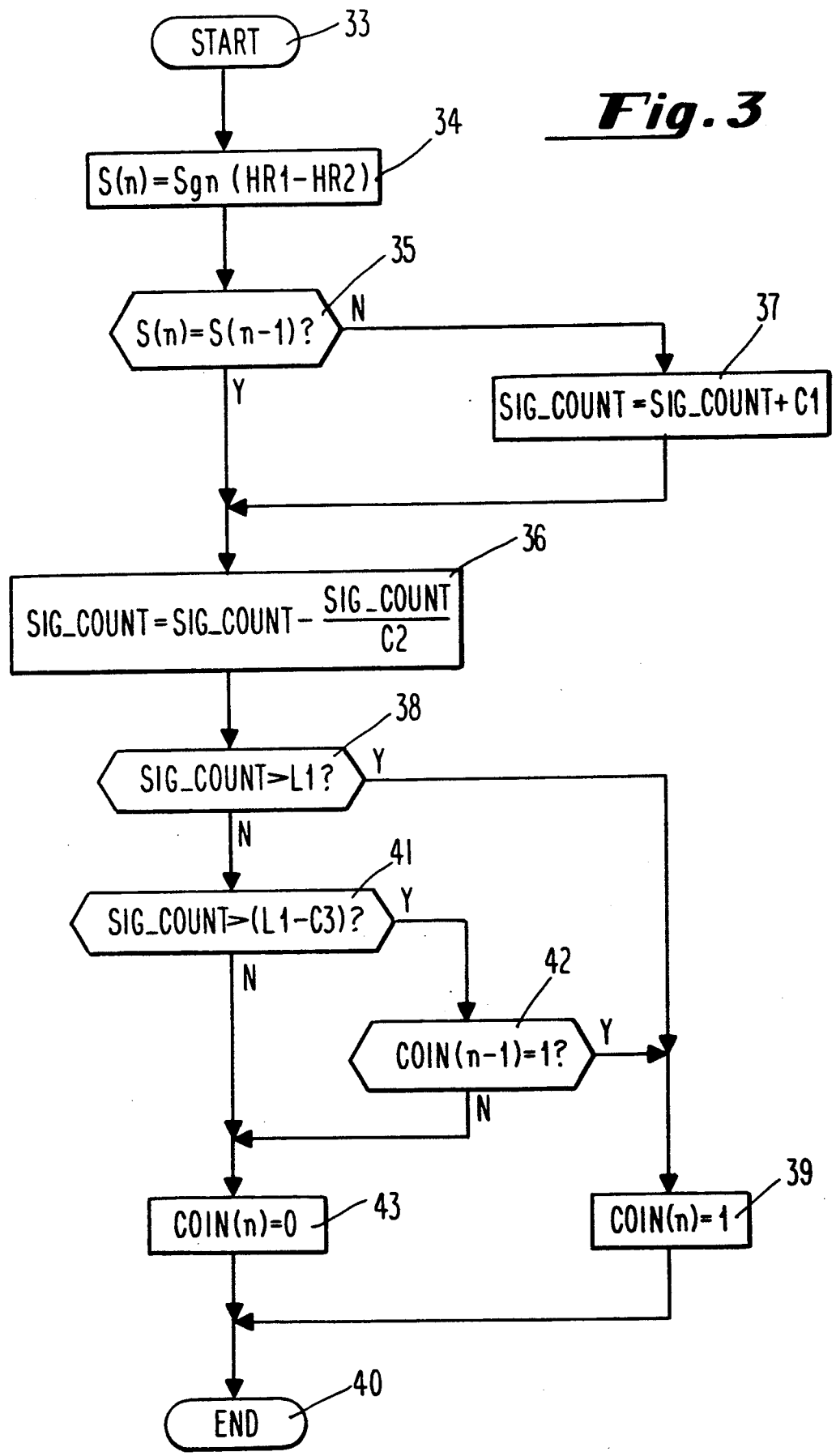

METHOD AND APPARATUS FOR PROCESSING HEART RATE TRACES IN A FETAL MONITOR

FIELD OF THE INVENTION

The present invention generally relates to methods and apparatuses for determining the heart rate of a fetus. The present invention more particularly relates to methods and apparatuses for processing signals indicative of two or more heart rates (e.g., of two fetuses or one fetus and its mother) to discriminate the respective beat-to-beat heart rates of the fetus(es).

BACKGROUND OF THE INVENTION

In gynecology and obstetrics, two medical parameters are important to assess the condition of the fetus. These two parameters are the fetal beat-to-beat heart rate and uterus (or labor) activity. Simultaneous assessment of the fetal heart rate (FHR) and uterus activity (toco) allows an exact determination of the fetal condition. Monitors measuring and recording both parameters are called "fetal monitors" or "cardiotocographs" (CTG monitors).

To obtain a signal indicative of the fetal heart rate, a so-called fetal scalp electrode may be applied to the fetal skin. These electrodes are usually spiral electrodes which are screwed into the fetal epidermis. See e.g., U.S. Pat. No. 3,827,428. Such direct electrodes allow very accurate measurements due to excellent signal quality. Unfortunately, such internal or direct measurement can only be used after rupture of the membranes. Prior to that point in time (in particular during gestation), indirect methods must be used. These indirect measurements are performed abdominally, e.g. by listening to the fetal heart sound or by measuring the Doppler shift of an ultrasound wave reflected by the moving parts of the fetal heart, particularly the heart walls and the heart valves. Further methods for recording the fetal heart rate employ electrocardiogram electrodes placed on the abdomen of the mother (the abdominal electrocardiogram), the registration of fetal heart sounds with a microphone ("Phono"), the oxygen saturation signal and the like. The present invention relates to all of these methods.

Neither the electrocardiogram, received ultrasound signal, or any other signal indicative of the fetal heart rate is of major diagnostic importance. What is in fact required to assess the fetal condition is the beat-to-beat heart rate. This means that heart beats must be detected in the above signals and the heart rate calculated as the inverse of the time interval between two consecutive beats. The detection of heartbeats and, in particular, the precise determination of the point in time when a beat occurs are difficult tasks. When ultrasound signals are used, many fetal monitors use an autocorrelation technique to detect heartbeats. An autocorrelation signal has a peak that provides an indication of the period of the autocorrelated signal itself. Therefore, it is possible to detect the occurrence of heartbeats even in very noisy signals; however, even the autocorrelation technique does not produce absolutely accurate values for the time interval between two heartbeats, due to the complexity of the received ultrasound signal. That is, even in the case of a silent heart rate, the heart rate trace produced by means of the autocorrelation technique will contain jitter (high-frequency components). This is also true if techniques other than autocorrelation are used; even a direct electrocardiogram obtained by means of a spiral electrode may contain jitter, particularly if the heart rate is high and the sampling rate low (e.g. 200 Hz).

A further problem encountered in fetal monitoring is to ensure that in fact the fetal heart rate and not the maternal heart rate is recorded. There may be several circumstances under which a fetal monitor records the maternal heart rate instead of the fetal one. For example, if an electrocardiogram signal is derived by means of a fetal scalp electrode and the fetus is dead, then the maternal ECG, and therefore the maternal heart rate, may erroneously be measured. The problem is even more serious when the heart rate is derived from an ultrasound signal. If the ultrasound transducer is not precisely focused on the fetal heart, other periodic signals from the mother, e.g. originating from the placenta or the maternal abdominal aorta, may be recorded. This may particularly happen if an autocorrelation technique is used, as this technique tends to lock on a particular signal once detected; i.e., if the algorithm erroneously triggers on the maternal heart rate instead of the fetal heart rate, it will lock on the maternal rate. It is also possible that, due to labor or movement of the fetus, the fetal heart will move away from the ultrasound beam.

The erroneous recording of the maternal heart rate trace instead of the fetal heart trace rate may cause false diagnosis or other dangerous consequences. In order to avoid these situations, a nurse or doctor may measure the maternal rate manually and compare it with an acoustic signal, written recording or optical heart rate indication generated by the fetal monitor. This requires the presence of a clinical person, and is therefore seldom done. Another method is to record the heart rate traces of the fetus and the mother and compare the traces. This method has the same disadvantage, i.e., it requires supervision.

Another problem arises if twins are being monitored—the fetal heart rates may be confused with the maternal heart rate, but also an interchange between the two fetal heart rate traces is possible; e.g., the heart rate trace of the first fetus may be recorded twice instead of the respective heart rate traces of the first and second fetuses.

An object of the present invention is to provide methods and apparatuses for determining the fetal heart rate that generate a reliable warning signal if a heart rate trace originating from the same subject is recorded twice (and thus another heart rate trace of interest is missed). A further object of the present invention is to provide methods and apparatuses, for determining the fetal heart rate, that need no manual supervision. The latter point is of particular importance as it has been observed that, due to a shortage of qualified personnel, manual counter-checks are not made on a regular basis in obstetrical care units.

SUMMARY OF THE INVENTION

A method, in accordance with the invention, for determining the heart rate of a fetus comprises the steps of obtaining a first signal indicative of fetal heart beats of a first fetus and a second signal indicative of fetal heart beats of second fetus and/or maternal heart beats of the mother, comparing the first signal with the second signal and producing a third signal indicative of the coincidence between the first and second signals, comparing the third signal to a limit, and generating a warning signal if the third signal bears a predefined relation to the limit.

In specific, preferred embodiments, the limit may be either a predefined limit or an adaptive limit. In addition, the first signal may be either directly or indirectly compared with the second signal.

The method may also include detecting crossings of the first signal with the second signal, counting the number of crossings, producing a count indicative of the number of crossings, and generating a warning signal if the number of crossings exceeds the limit. The method in this embodiment may also comprise the step of reducing the count by a predetermined factor in either predetermined or adaptive time intervals. In addition, the number of crossings may be counted over either predefined or adaptive time intervals.

The method may also include the steps of comparing the third signal to a second limit, generating the warning signal if the number of crossings exceeds the higher of the limits, and stopping the generation of the warning signal if the number of crossings falls below the lower of the limits.

In still another embodiment, the method may further include the steps of computing the difference between the first signal and the second signal and comparing the absolute value of the difference against the limit. This embodiment may also include the steps of summing absolute values of the differences between the first and second signals taken at a plurality of instances, and reducing the sum by a predetermined factor. In this case the warning signal is generated if the sum falls below the limit. In addition, the sum may be reduced by the predetermined factor in either adaptive or predetermined time intervals.

In another embodiment, the method further comprises the steps of summing absolute values of the differences between the first and second signals during either an adaptive of predetermined time window. In this case the warning signal is generated if the sum falls below the limit.

In yet another embodiment the first and second signals are cross-correlated with each other to produce a correlation function, and the warning signal is generated if the correlation function exceeds the limit. This embodiment may also include the steps of comparing the correlation function with a second limit, generating the warning signal if the correlation function exceeds the higher of the limits, and stopping the generation of the warning signal if the correlation function falls below the lower of the limits.

The present invention also encompasses a method for determining the respective fetal heart rates of two fetuses. This method comprises the steps of obtaining a first signal indicative of fetal heart beats of a first fetus and a second signal indicative of fetal heart beats of a second fetus, processing one of the first and second signals with an adaptive filter with variable filter coefficients to obtain an output signal, comparing the output signal with the other of the first and second signals and generating a difference signal based upon the comparison, adapting the filter coefficients so that the difference signal is minimized, and generating a warning signal if a sum of one or more of the filter coefficients bears a predefined relation to a limit.

A further method provided by the present invention for determining the respective fetal heart rates of two fetuses comprises the steps of obtaining a first signal indicative of fetal heart beats of a first fetus and a second signal indicative of fetal heart beats of a second fetus, cross correlating the first and second signals with each other to produce a correlation function, and generating a warning signal if the correlation function exceeds a limit.

The first signal in any of the foregoing methods is most preferably derived from an ultrasound signal. In this case the method may also further include focusing the ultrasound signal in response to the warning signal.

The present invention also encompasses apparatuses for carrying out the foregoing methods. One example of such an apparatus includes difference calculation means for calculating the difference between the first and second signals, means for determining the sign of the difference and means for counting the number of sign changes. This embodiment may also include averaging means for averaging the number of sign changes. The averaging means may comprise, e.g., means for computing either an exponential average or a moving average.

Another embodiment of the invention further comprises means for obtaining an alternate signal indicative of heart beats of at least one of the first and second fetuses, and switching means for switching to a different combination of the first, second and alternate signals in response to the warning signal.

The apparatus may also include hysteresis means for avoiding jitter in the warning signal.

BRIEF DESCRIPTION OF THE DRAWINGS

FIG. 3 is a flowchart outlining the operation of the apparatus of FIG. 2.

DETAILED DESCRIPTION OF THE PREFERRED EMBODIMENTS

The invention will now be explained by means of non-limiting examples, with reference to the accompanying drawings.

Figure 1:
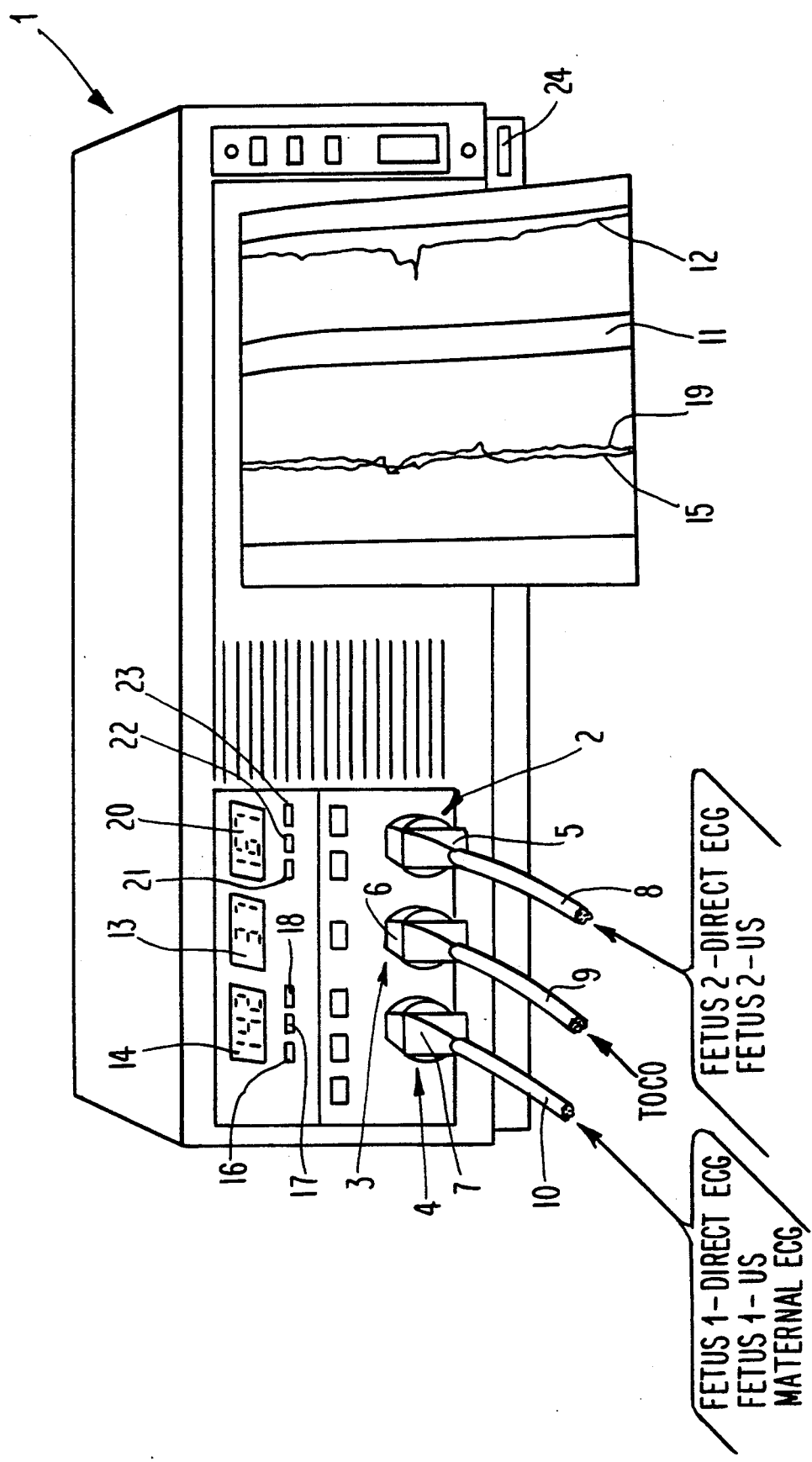
FIG. 1 depicts a perspective view of a fetal monitor.

FIG. 1 depicts a fetal monitor used to monitor the heart rate of a fetus during pregnancy and labor, and to record uterus (or labor) activity. Simultaneous assessment of the fetal heart rate and uterus activity allows a precise determination of the fetal condition. Fetal monitor 1 comprises three jacks 2, 3, 4 for the insertion of appropriate connectors 5, 6, 7. These connectors are linked via cables 8, 9, 10 to corresponding transducers (not shown here). Jack 3 is an inlet for the toco (uterus activity) transducer. Although this is an important parameter for the assessment of the fetal condition, it is not a subject of the present invention and is therefore not discussed in detail herein. The signal measured via the toco channel is recorded on a thermal printer which is built into the monitor 1. Paper 11 is used by the thermal printer to record the parameter traces. The toco recording is denoted as 12. Further, the measured toco value is optically indicated by means of display 13, a combination of 7-segment displays.

Jack 4 is an inlet for the fetal heart activity signal. Two different connectors 7 may be used. After rupture of the membrane (during second-stage labor and birth) a fetal scalp electrode, which is applied intravaginally, may be used. Although this method (called "direct ECG") yields excellent results, it cannot be used in pre-birth applications and during pregnancy. In these cases another transducer must be used, namely an ultrasound (US) transducer. The ultrasound transducer emits bursts of high-frequency ultrasound waves and receives the ultrasound signals reflected by the maternal or fetal tissue and bones. The frequency of the reflected ultrasound waves is shifted with respect to their original frequency due to the Doppler effect. A demodulator with subsequent filters is used to obtain the Doppler signal. Peaks in the Doppler signal are indicative of a fetal heart beat; however, since the Doppler signal is usually quite noisy, additional measures must be taken to facilitate detection of a peak. The fetal monitor depicted in FIG. 1 uses an autocorrelation mechanism therefor.

Regardless of whether the fetal heartbeat is obtained by means of a scalp electrode or an ultrasound transducer, the fetal heart rate is calculated as the inverse of the time interval between two successive heart beats. This is an important feature of the fetal monitor since the beat-to-beat heart rate provides valuable diagnostic information.

The detected fetal heart rate is displayed by means of a 7-segment display 14 and recorded on the thermal printer as heart rate trace 15. Backlighting modules 16, 17 and 18 indicate the quality of the signal used for fetal heart rate detection. Module 16 is a red module, module 17 a yellow module and module 18 a green module. As long as the received signal is of good quality, green module 18 is on. When the signal is of worse quality, i.e. heartbeat detection becomes questionable, yellow module 17 is switched on, and green module 18 is switched off. When no fetal beat-to-beat heart rate trace can be recorded, red module 16 indicates poor signal quality.

Jack 7 may also provide a maternal electrocardiogram signal obtained, e.g., by ECG electrodes, a plethysmographic transducer or the like. If this signal is provided, the maternal heart rate trace is also recorded as trace 19. The maternal heart rate may be calculated from beat to beat, but it may also be calculated over longer time intervals.

Fetal monitor 1 further provides a third jack 2 for the insertion of a corresponding connector 5. The latter is connected via cable 8 with a second fetal transducer, namely a second fetal scalp electrode or a second ultrasound Doppler transducer. These transducers are used in the case of twins to obtain a fetal beat-to-beat heart rate trace of the second fetus. If a second fetal transducer is connected, the beat-to-beat heart rate of the second fetus is recorded as trace 19 instead of the maternal heart rate trace. A display 20 indicates the value of the second fetal heart rate and backlighting modules 21, 22 and 23 indicate the quality of the second fetal signal. It is understood that the fetal monitor is not limited to recording only two heart rate traces on the internal printer, but may also record three or more heart rate traces, e.g., if signals indicative of the heart beats of a first fetus, a second fetus and the mother are fed to the monitor. Other components of fetal monitor 1, such as the power-on button 24, are well known and therefore are not discussed herein.

The fetal monitor 1 is able to compare two heart rate traces and provide a warning whenever coincidence between the heart rate traces is detected. This important clinical information indicates that, e.g., two transducers are inadvertently focused on the same fetal heart or a fetal transducer is detecting signals originating from the maternal placenta or the maternal abdominal aorta. E.g., if a fetal ultrasound transducer is connected as well as maternal ECG electrodes, coincidence between the corresponding heart rate traces is an indication that both transducers are recording the maternal heart rate and that the fetal heart is not being monitored; thus a dangerous condition, such as insufficient oxygen supply to the fetus, would not be detected.

Another situation where the maternal heart trace is recorded instead of fetal heart trace is when the ultrasound Doppler signal contains a weak component due to the fetal heart and strong components due to the mother. In such cases an autocorrelation algorithm will take the maternal heart rate. Even if the fetal signal becomes stronger, the autocorrelation algorithm tends to stay locked on the maternal signal.

Fetal monitor 1 is able to detect coincidence between the fetal and the maternal heart rate signals. Further, if a second fetal transducer is connected, coincidence checks are made between the second fetal heart rate trace and the maternal heart rate trace, and also between the first fetal heart rate trace and the second fetal heart rate trace. The appropriate backlighting modules are switched to red whenever coincidence is detected. In addition, a warning item is printed on the recorder (as explained below with reference to FIG. 5). Furthermore, a warning signal is fed to a system connector (not shown in FIG. 1) so that a central station connected to the fetal monitor may record it. An acoustic alarm or the like may also be generated.

Figure 2:
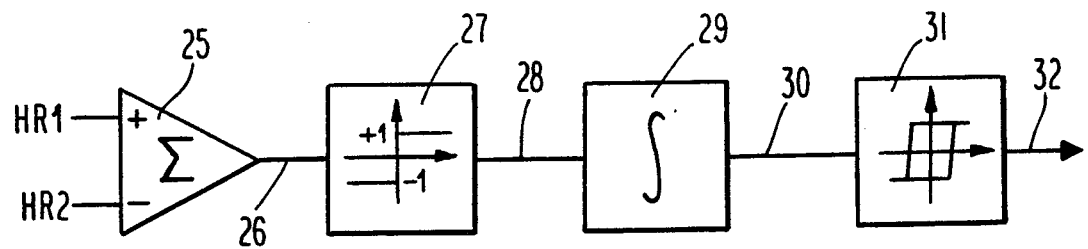
FIG. 2 is a block diagram of an apparatus for performing coincidence detection in accordance with the present invention.

FIG. 2 is a block diagram of a first embodiment of an apparatus for providing coincidence detection. Two heart rate signals HR1 and HR2 are fed to a summing circuit 25. HR1 is fed to a positive input terminal and HR2 to a negative input terminal of summing circuit 25; thus the summing circuit generates a difference signal on line 26. Heart rate signals HR1 and HR2 may be any combination of the heart rate traces of a first fetus, a second fetus and the mother.

The difference signal 26 is fed to a signum generator 27. The signum generator determines the sign of the difference signal according to the following equation:

$$s = \operatorname{signum}(d) = \begin{matrix} -1 \text{ for } d < 0 \\ +1 \text{ for } d \geq 0 \end{matrix} \quad . \tag{1}$$

wherein d is the difference signal at the input of the signum generator and s is the signum signal on line 28, i.e., the output of the signum generator.

The definition of the signum function given above is different from its definition in mathematical science insofar as the signum function is +1 and not zero when the difference signal equals zero. This is because signum generator 27 is designed to count sign changes, i.e., crossings of the two heart rates. It is understood that the operation of the signum generator could also be defined in a different manner, e.g., as $$s = \text{signum}(d) = \begin{cases} -1 \text{ for } d \leq 0 \\ +1 \text{ for } d > 0 \end{cases} \quad (2)$$

or $$s(n) = \text{Signum}(d(n)) = \begin{cases} -1 \text{ for } d(n) < 0 \\ s(n-1) \text{ for } d(n) = 0 \\ +1 \text{ for } d(n) > 0 \end{cases} \quad (3)$$

wherein n is the index number of the samples.

A further possibility is to count a difference of zero as a sign change (provided the previous difference has not also been zero) and to determine whether the difference signal continues to move in the same direction (in which case no further sign change is recorded). It is also possible to count every difference of zero as a sign change. This is particularly useful if the two heart rate signals contain little or no jitter.

The signum signal on line 28 is fed to an integrator 29. The integrator serves two different functions: first, it integrates (sums) the sign changes; second, it ensures that the integral or the sum of the sign changes does not increase without limitation (i.e., its output decreases slightly if no further sign changes occur). There are two basic ways to implement the second function. The first is to calculate the integral from a finite lower limit which moves with the current point in time to an upper limit which equals the current point in time. In digital terms this means that the sum is calculated from a moving lower limit to an upper limit which equals the current sample, e.g., according to the following equation:

$$\text{sum} = \sum_{v=n-c}^{v=n} s(v) \quad (4)$$

wherein "sum" is the output of the integrating circuit, n is the current index and c is a constant. Due to the moving lower limit of the integral or the sum, the resulting average is also called a "moving" or "sliding" average.

The alternative is an exponentially decreasing average, wherein the sum is reduced by a certain factor each time a new calculation is made, e.g., according to the equation $$\text{sum}(n) = \text{sum}(n-1) - \frac{\text{sum}(n-1)}{c} + \frac{s(n)}{c} \quad (5)$$

The output of integrator 29 is fed via line 30 to a comparator 31. The function of the comparator is to compare the output of integrator 29 with a predefined or adaptive limit and to generate a warning signal at its output line 32 if the integrated signal exceeds a certain limit, i.e., if sign changes of a significant frequency have been observed. To prevent the warning signal from changing its state too rapidly, e.g. if the sum of the sign changes crosses the limit many times within a short time interval, comparator 31 provides a hysteresis function which is explained in more detail below with reference to FIG. 3.

The warning signal on line 32 may be fed to any appropriate warning means, e.g., means for providing an optical or acoustic alarm, means for providing an annotation on a printer or recorder, or means for adjusting the ultrasound beam when an adjustable ultrasound Doppler transducer is used, e.g., when a transducer with controllable depth selection is used.

In the embodiment of FIG. 2 a special property of the heart rate traces is used for the detection of coincidence between two heart rates, namely that the traces contain a high-frequency component, or "jitter." This jitter is due to both physiological causes and the signal processing algorithm used in the fetal monitor. In particular, the extent of the Doppler signal representing the movement of the fetal heart walls and heart valves is quite long, so that its start and end points cannot be determined precisely in time. This leads to inaccurate beat-to-beat heart rates, and therefore to a jitter signal superimposed on the heart rate trace. Likewise, if a scalp electrode is used, the heart rate is high, and the sampling frequency is in the range of 200 Hz or less, the QRS complexes in the direct electrocardiogram cannot be precisely defined in time, thus causing jitter.

The present invention makes use of the jitter in the heart rate trace. The inventor has observed that heart rate traces originating from the same person comprise a significant number of crossings, i.e., sign changes, of the difference signal; therefore, the frequency of sign changes of the difference signal is an indication of coincidence. If the jitter is not sufficient to trigger the signum generator sufficiently frequently, e.g., in the case of a silent heart rate trace or if one heart rate has a constant offset, an artificial jitter signal can be superimposed on one or both of the heart rate traces. Further optimization can be obtained by additional filters, delay elements for the compensation of different processing times and variation of tolerance windows.

The operation of the coincidence detection circuit shown in FIG. 2 will now be explained with reference to FIG. 3, which explains how the individual components of FIG. 2 operate or, if a microprocessor-based system is used, describes the operation of a subroutine executed periodically.

After entering the flowchart at the "START" label 33, s(n) is calculated as the signum function of the difference between two heart rate traces HR1 and HR2 (step 34). Heart rate traces HR1 and HR2 are obtained from a fetus and the mother. If twins are monitored, these could also be heart rate traces from a first fetus and a second fetus, or from a second fetus and the mother. If signals from two fetuses and a mother are processed, the subroutine in FIG. 3 is executed for all possible combinations of these signals, i.e., fetus 1/mother, fetus 1/fetus 2 and fetus 2/mother. The fetal heart rate traces are beat-to-beat heart rates; the maternal heart rate may be a beat-to-beat heart rate or a heart rate calculated on the basis of a longer time constant.

The signum function calculated in step 34 is then compared with the sign of the previous difference (step 35). If the signs are equal, operation proceeds to step 36. If not, a variable SIG_COUNT is increased by a constant C1 (step 37).

In step 36 the variable SIG_COUNT, which is indicative of the frequency of the sign changes, is reduced in accordance with a predetermined factor C2. Thus an exponential average of SIG_COUNT is taken, although a moving average can be used as well.

The calculated value of SIG_COUNT is then compared with a first limit L1 (step 38). If SIG_COUNT exceeds this limit, a coincidence indicator COIN(n), which operates as a warning signal, is set to 1 (step 39) and operation stops (step 40).

If SIG_COUNT has not exceeded limit L1, it is further checked against a second, lower limit L1-C3 (step 41). If the second limit is exceeded, i.e., the value of SIG_COUNT is between the upper and the lower limits, a further check is made to see whether the warning signal COIN(n-1) is set (step 42). If so, the warning signal is kept in its "true" state in order to avoid jitter of the warning signal caused by a minimal decrease of SIG_COUNT, i.e, COIN(n) is set to 1 (step 39). Note that steps 41 and 42 implement the hysteresis function mentioned above.

If variable SIG_COUNT does not exceed either of the limits, or if only the lower limit is exceeded without a warning signal having been generated during the previous cycle, coincidence warning signal COIN(n) is set to zero (step 43), and execution stops.

The operation of the coincidence detector described in FIGS. 2 and 3 will now be explained with reference to the exemplary traces depicted in FIG. 4. The upper diagram depicts two beat-to-beat heart rate traces originating from two fetuses. The horizontal axis denotes the time. The next diagram depicts the trace 45 of variable SIG_COUNT. In this example the upper limit L1 has been set to 6 and the lower limit L1-C3 has been set to 4. The values of SIG_COUNT are real numbers in the example, however integers are preferable if a microcomputer is used.

Figure 4:
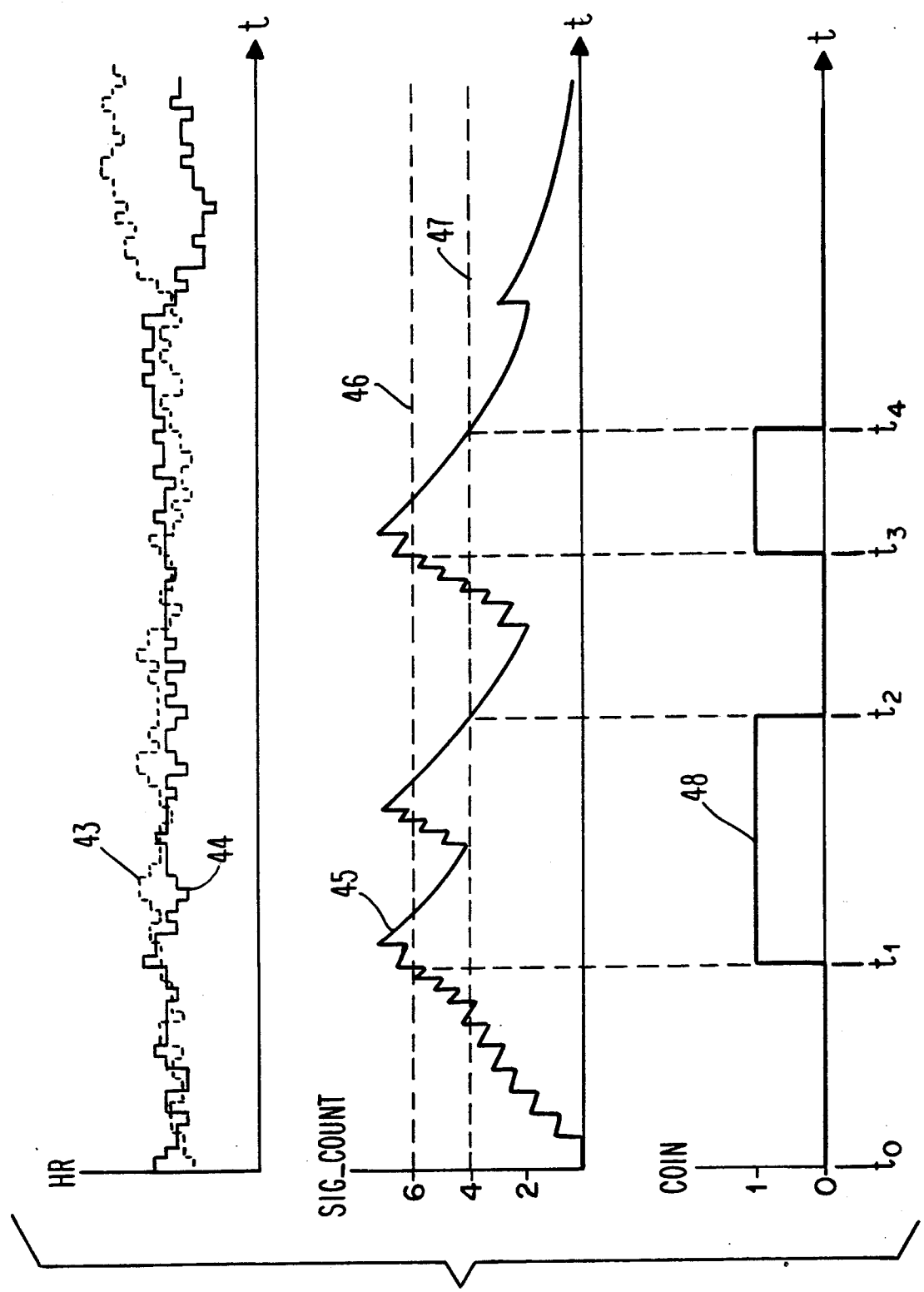
FIG. 4 depicts timing diagrams of two heart rate traces, an intermediate sign counting variable and the coincidence indicator of the apparatus of FIG. 2.

The diagram at the bottom of FIG. 4 depicts the trace 48 of the coincidence warning signal COIN over time. During a first time period ($t_0 < t < t_1$) several crossovers of the two heart rate traces 43, 44 occur; however, although variable SIG_COUNT is increasing, it has not yet reached the limit L1 and therefore no warning signal is generated. The upper limit is exceeded at $t = t_1$ and the warning signal is turned on. Although the value of the SIG_COUNT returns to the lower limit and then exceeds the upper limit again, the warning signal remains on. This is caused by the hysteresis function provided by the comparator, which prevents the warning signal from being switched on and off too frequently.

At $t = t_2$ the value of SIG_COUNT crosses the lower limit and the warning signal is turned off. This is caused by the fact that the heart rate traces 43 and 44 do not cross around $t = t_2$. Due to the averaging function, the value of SIG_COUNT is therefore reduced. When crossings again occur, the value of SIG_COUNT exceeds the upper limit and the warning signal is turned on at $t = t_3$. After this point in time the two heart rate traces depart from each other, so that at $t = t_4$ the coincidence warning signal is turned off again.

Figure 5:
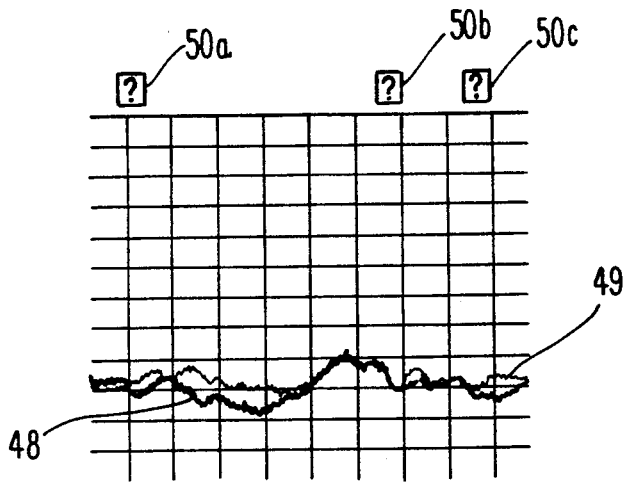
FIG. 5 depicts a print-out of a fetal monitor illustrating coincidence detection.

FIG. 5 depicts an exemplary printout on the thermal printer of a fetal monitor. Whenever a significant number of crossings of the two heart rate traces 48, 49 has been detected, a question mark is printed (references numbers 50a, 50b, 50c) to indicate possible coincidence.

Figure 6:
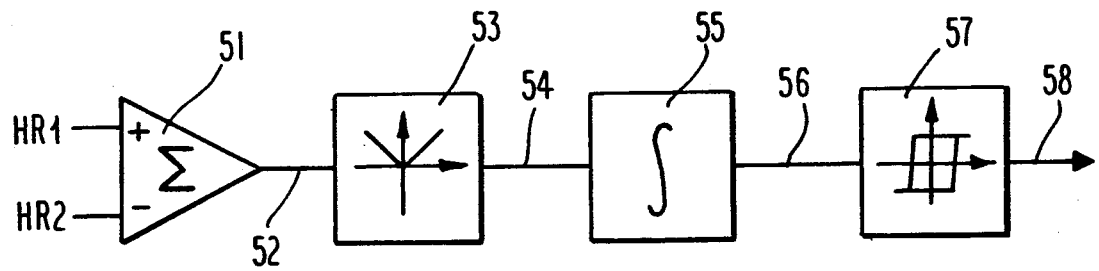
FIG. 6 is a block diagram of a second apparatus for performing coincidence detection in accordance with the present invention.

Another embodiment of the present invention is shown in FIG. 6. Again, as in FIG. 2, the two heart rate traces HR1 and HR2 are fed to a summing circuit 51 which calculates the difference between the two heart rate traces. The signal on line 52 is fed to an absolute value generator 53, which simply converts a negative sign of the difference into a positive sign. The signal is then fed via line 54 to an integrator 55 and then via line 56 to a comparison circuit 57, thus generating an output signal on line 58. Integrator 55 and comparison circuit 57 are similar to elements 29 and 31 in FIG. 2. The major difference between the circuits depicted in FIGS. 2 and 6 is that, in the environment of FIG. 6, an absolute value generator is used instead of a signum generator. The circuit of FIG. 6 actually calculates the area between the two heart rate traces. Preferably, the heart rate traces fed to the circuit of FIG. 6 are pre-filtered, or averaged, to avoid errors caused by jitter.

Figure 7:
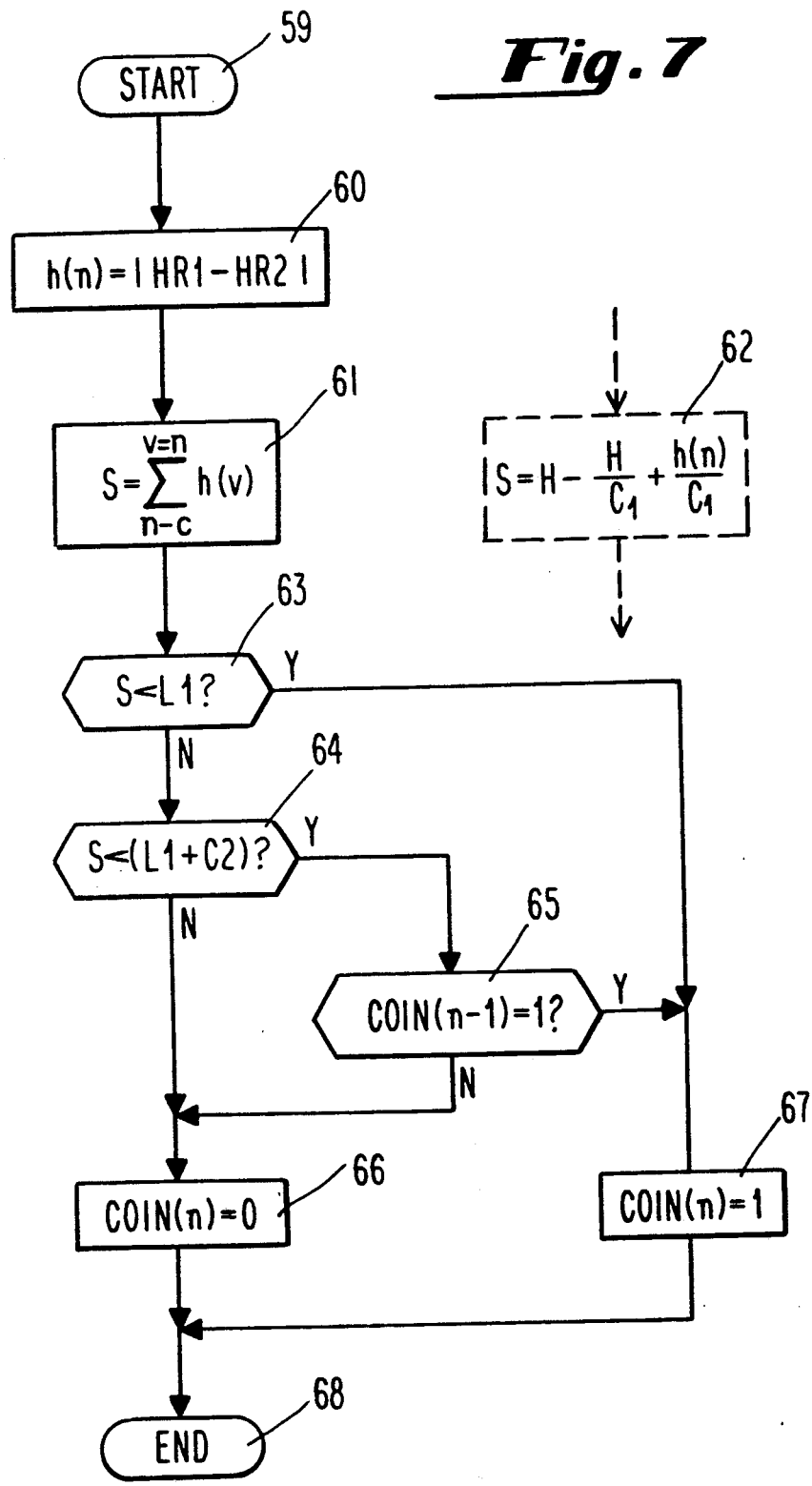
FIG. 7 is a flowchart outlining the operation of the apparatus of FIG. 6.

Operation of the circuit depicted in FIG. 6 will now be explained with reference to the flowchart shown in FIG. 7. If a microprocessor is used to perform the necessary calculations, this flowchart represents a subroutine which is executed on a periodic basis.

Operation starts at label "START," reference numeral 59. Variable h(n) is then calculated as the absolute value of the difference between heart rate traces HR1 and HR2 (step 60). Operation then proceeds to step 61, in which a sliding average is calculated over c samples (see equation (4)). Step 62 depicts an alternative embodiment wherein an exponential average is calculated, i.e., step 61 could be replaced by step 62.

Steps 63, 64 and 65 implement a hysteresis function. Reference is made to the corresponding steps 38, 41 and 42 of FIG. 3. Depending on the result of these comparisons, the coincidence warning signal is either set to 0 (step 66) or 1 (step 67). Operation stops at step 68.

Figures 8, 9:
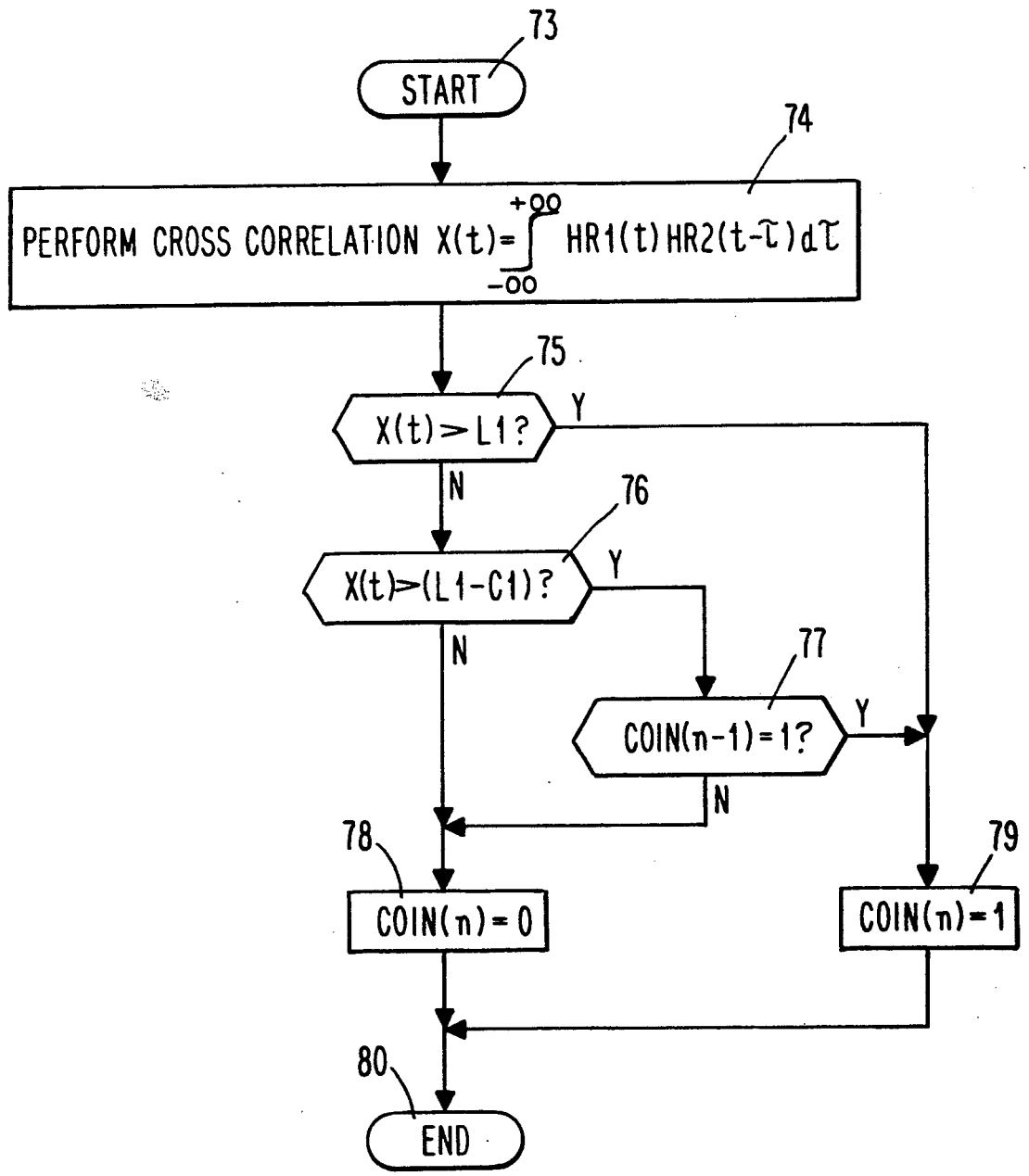
FIG. 8 depicts a third apparatus for performing coincidence detection in accordance with the present invention.
FIG. 9 is a flowchart outlining the operation of the apparatus of FIG. 8.

A further embodiment of the invention is depicted in FIGS. 8 and 9. As shown in FIG. 8, the two heart rate traces HR1, HR2 are fed to a cross-correlator 69. The amplitude of the output of the cross-correlator on line 70 is fed to a comparison circuit 71, which generates an output on line 72. The output of the cross-correlator provides an indication of the correlation between the two heart rate signals. That is, the higher the amplitude of the cross-correlation signal, the higher the correlation (or coincidence) between the two heart rate signals.

FIG. 8 depicts only a typical example of how cross-correlation may be used to detect coincidence between the heart rate signals. Other embodiments may be used as well; e.g., the raw (unprocessed) signals received from ultrasound transducers or ECG probes could be directly fed to a cross-correlation circuit, without heart rate generation or other pre-processing. Although this solution saves processing time, it requires a considerably higher sampling frequency and therefore a faster cross-correlator.

Operation of the circuit depicted in FIG. 8 will now be explained with reference to FIG. 9. Again, this flowchart represents operation of corresponding analog or digital circuitry, or the operation of a microprocessor. In the latter case, the microprocessor executes the associated subroutine on a periodic basis.

After entering the subroutine at label "START," reference numeral 73, a cross-correlation is performed between the two time-dependent heart rate traces HR1(t) and HR2(t) in accordance with the equation shown at step 74. It should be noted that this equation represents the operation of an ideal cross-correlator. Actual cross-correlators do not take the integral from negative to positive infinity; they use the sum instead of the integral and the summing limits are finite values.

The result of the cross-correlation is a function X(t) the amplitude of which is indicative of the correlation or coincidence between the two incoming signals. The correlation signal X(t) is then compared with upper and lower limits (L1 and L1-C1) to implement a hysteresis function (steps 75 to 77). Depending upon the results of these comparisons, the coincidence warning signal is then either set to 0 (step 78) or 1 (step 79). Operation stops at step 80.

Figure 10:
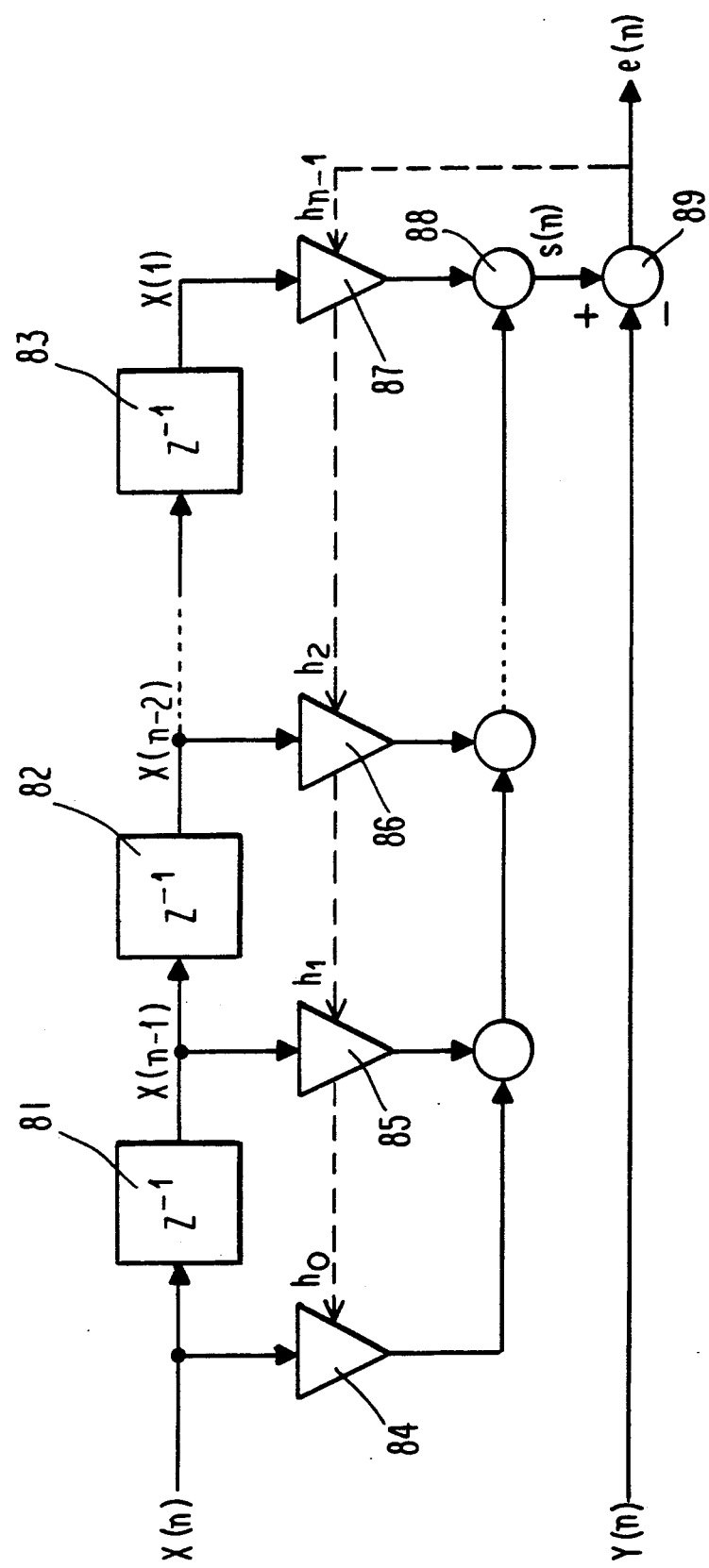
FIG. 10 is a block diagram of an adaptive filter.

FIG. 10 depicts a block diagram of an adaptive filter used for coincidence detection. The digitized samples of a first ultrasound signal X(n) are fed to the filter with a multiplicity of delay circuits 81, 82 and 83 (the dotted line between elements 82 and 83 indicates that there might be further delay circuits). Before the first and after every delay circuit, the signal is fed, via amplifiers 84 to 87 with adjustable (adaptive) gain, to a summing point 88. The difference between the sum of all these signals and the second heart rate trace Y(n) is calculated at element 89, thus generating a signal e(n). The weighting factors (or gain) $h_0, h_1, h_2 \ldots h_{n-1}$ of the variable amplifiers are controlled in accordance with e(n).

The output s(n) of the digital filter, is given by $$s(n) = h_0 x(n) + h_1 x(n-1) + \ldots + h_{n-1} x(n - (n-1)) \quad (6)$$
$$= h_0 x(n) + h_1 x(n-1) + \ldots + h_{n-1} x(1)$$

with x(n) being the first ultrasound signal and $h_0 \ldots h_{n-1}$ being the variable filter coefficients. The difference from the second ultrasound signal y(n) is $$e(n) = s(n) - y(n) \quad (7)$$

The filter coefficients can be calculated by the following recursion formula:

$$h_i(n+1) = h_i(n) + 2k \cdot e(n) \cdot x(n-i) \quad (8)$$

wherein k is a constant selected on the basis of the particular application. The filter coefficients are periodically optimized so that the output of the filter approaches the second ultrasound signal; i.e., so that the difference signal e(n) is minimized. If the two ultrasound signals are approximately equal, the filter coefficients become stable and may be used to determine the phase between the two ultrasound signals. If the ultrasound signals are equal, the phase is constant. Therefore the filter coefficients can be used to determine whether the two ultrasound signals are coincident. The final determination can be made in a comparison circuit as described in the previous examples. The adaptive filter method yields the best results when the two ultrasound signals comprise little jitter. The embodiment depicted in FIG. 10 is particularly useful if raw (unprocessed) ultrasound signals are evaluated; however the heart rate traces could be processed in the same or a similar manner.

Another embodiment of the invention, not shown in the drawings, uses the difference or the absolute value of the difference between the two heart rate traces to determine coincidence. This difference may be compared with the predefined or adaptive limit and may also comprise a hysteresis function. This method is particularly useful when direct electrocardiograms are processed. Ultrasound transducers with adjustable, or adaptive, characteristics are already available on the market. For example, the ultrasound transducer may be able to search, on an automatic basis, for the correct depth where the fetal heart can be found. A transducer of this kind is described in European patent application EP-A-204 192. If such an automatic ultrasound transducer is used, the warning signal may advantageously be used to start a new search cycle, i.e., to search for another physiological object. This means that once a suspected coincidence is detected, the fetal monitor automatically searches for the fetal heart to detect a heart rate signal that is not coincident with another one. Many other variations and modifications of the above-described specific embodiments of the invention will be apparent to those skilled in the art. The following claims are intended to cover all such embodiments.

What is claimed is:

1. A method for determining the hear rate of a fetus, comprising the steps of:
    (a) obtaining a first signal indicative of the fetal heat rate of a first fetus and a second signal indicative of the fetal heart rate of a second fetus and/or the maternal heart rate of the mother of said first fetus;
    (b) comparing said first signal with said second signal and producing a third signal indicative of the coincidence between said first and second signals;
    (c) comparing said third signal to a limit; and
    (d) generating a warning signal if said third signal bears a predefined relation to said limit.

2. The method recited in claim 1, wherein said limit is a predefined limit.

3. The method recited in claim 1, wherein said limit is an adaptive limit.

4. The method recited in claim 1, wherein step (b) comprises directly comparing said first signal with said second signal.

5. The method recited in claim 1, wherein step (b) comprises indirectly comparing said first signal with said second signal.

6. The method recited in claim 1, wherein step (b) comprises the steps of detecting crossings of said first signal with said second signal, counting the number of crossings and producing a count indicative of the number of crossings and, step (d) comprises generating said warning signal if the number of crossings exceeds said limit.

7. The method recited in claim 6, further comprising the step of reducing the count by a predetermined factor in predetermined time intervals.

8. The method recited in claim 6, further comprising the step of reducing the count by a predetermined factor in adaptive time intervals.

9. The method recited in claim 6, wherein the number of crossings is counted over predefined time intervals.

10. The method recited in claim 6, wherein the number of crossings is counted over adaptive time intervals.

11. The method recited in claim 6, further comprising the steps of comparing said third signal to a second limit, generating said warning signal if the number of crossings exceeds the higher of said limits, and stopping the generation of said warning signal if the number of crossings falls below the lower of said limits.

12. The method recited in claim 1, further comprising the steps of computing the difference between said first signal and said second signal and comparing the absolute value of said difference against said limit.

13. The method recited in claim 12, further comprising the steps of summing absolute values of the differences between said first and second signals taken at a plurality of instances, and reducing the sum by a predetermined factor, said warning signal being generated if said sum falls below said limit.

14. The method recited in claim 13, wherein said sum is reduced by said predetermined factor in adaptive time intervals.

15. The method recited in claim 12, further comprising the steps of summing absolute values of the differences between said first and second signals during a time window, said warning signal being generated if said sum falls below said limit.

16. The method recited in claim 15, wherein said time window is an adaptive time window.

17. The method recited in claim 13 or 15, further comprising comparing said sum with a second limit, generating said warning signal if said sum falls below the lower of said limits, and stopping the generation of said warning signal if said sum exceeds the higher of said limits.

18. The method recited in claim 1, wherein said first and second signals are cross-correlated with each other to produce a correlation function, and said warning signal is generated if said correlation function exceeds said limit.

19. The method recited in claim 18, further comprising comparing said correlation function with a second limit, generating said warning signal if said correlation function exceeds the higher of said limits, and stopping the generation of said warning signal if the correlation function falls below the lower of said limits.

20. A method for determining the respective fetal heart rates of two fetuses, comprising the steps of:
   (a) obtaining a first signal indicative of fetal heart beats of a first fetus and a second signal indicative of fetal heart beats of a second fetus;
   (b) processing one of said first and second signals with an adaptive filter with variable filter coefficients to obtain an output signal;
   (c) comparing said output signal with the other of said first and second signals and generating a difference signal based upon the comparison;
   (d) adapting said filter coefficients so that said difference signal is minimized; and
   (e) generating a warning signal if a sum of one or more of said filter coefficients bears a predefined relation to a limit.

21. A method for determining the respective fetal heart rates of two fetuses, comprising the steps of:
   (a) obtaining a first signal indicative of fetal heart beats of a first fetus and a second signal indicative of fetal heart beats of a second fetus;
   (b) cross correlating said first and second signals with each other to produce a correlation function; and
   (c) generating a warning signal if said correlation function exceeds a limit.

22. The method recited in claim 1, 20 or 21, wherein said first signal is derived from an ultrasound signal, and further comprising focusing the ultrasound signal in response to said warning signal.

23. An apparatus for determining the heart rate of a fetus, comprising:
   (a) means for obtaining a first signal indicative of the fetal heart rate of a first fetus and a second signal indicative of the fetal heart rate of a second fetus and/or the maternal heart rate of the mother of said first fetus;
   (b) first comparison means for comparing said first signal with said second signal and producing a third signal indicative of the coincidence between said first and second signals;
   (c) means for comparing said third signal to a limit; and
   (d) means for generating a warning signal if said third signal bears a predefined relation to said limit.

24. The apparatus recited in claim 23, wherein said first comparison means comprises difference calculation means for calculating the difference between said first and second signals, means for determining the sign of said difference and counter means for counting the number of sign changes.

25. The apparatus recited in claim 24, further comprising averaging means for averaging the number of sign changes.

26. The apparatus recited in claim 25, wherein said averaging means comprises means for computing an exponential average.

27. The apparatus recited in claim 25, wherein said averaging means comprises means for computing a moving average.

28. An apparatus for determining the respective fetal heart rates of two fetuses, comprising:
   (a) means for obtaining a first signal indicative of the fetal heart rate of a first fetus and a second signal indicative of the fetal heart rate of a second fetus;
   (b) means for processing one of said first and second signals with an adaptive filter with variable filter coefficients to obtain an output signal;
   (c) means for comparing said output signal with the other of said first and second signals and generating a difference signal based upon the comparison;
   (d) means for adapting said filter coefficients so that said difference signal is minimized; and
   (e) means for generating a warning signal if a sum of one or more of said filter coefficients bears a predefined relation to a limit.

29. An apparatus for determining the respective fetal heart rates of two fetuses, comprising:
   (a) means for obtaining a first signal indicative of fetal heart beats of a first fetus and a second signal indicative of fetal heart beats of a second fetus;
   (b) means for cross correlating said first and second signals with each other to produce a correlation function; and
   (c) means for generating a warning signal if said correlation function exceeds a limit.

30. The apparatus recited in claim 23, 28 or 29, wherein said first signal is derived from an ultrasound signal, and further comprising means for focusing the ultrasound signal in response to said warning signal.

31. The apparatus recited in claim 23, 28 or 29, further comprising means for obtaining an alternate signal indicative of heart beats of at least one of said first and second fetuses, and switching means for switching to a different combination of said first, second and alternate signals in response to said warning signal.

32. The apparatus recited in any one of claims 23 to 31, further comprising hysteresis means for avoiding jitter in said warning signal.

33. A method for determining the heart rate of a fetus, comprising the steps of:
   (a) obtaining a first signal indicative of fetal heart beats of a first fetus and a second signal indicative of fetal heart beats of a second fetus and/or maternal heart beats;
   (b) detecting crossings of said first signal with said second signal, counting the number of crossings and producing a count indicative of the number of crossings;
   (c) comparing said count to a limit; and
   (d) generating a warning signal if said count bears a predefined relation to said limit.

34. The method recited in claim 33, further comprising the step of reducing the count by a predetermined factor in predetermined time intervals.

35. The method recited in claim 33, further comprising the step of reducing the count by a predetermined factor in adaptive time intervals.

36. The method recited in claim 33, wherein the number of crossings is counted over predefined time intervals.

37. The method recited in claim 33, wherein the number of crossings is counted over adaptive time intervals.

38. The method recited in claim 33, further comprising the steps of comparing said count to a second limit, generating said warning signal if the count exceeds the higher of said limits, and stopping the generation of said warning signal if the count falls below the lower of said limits.

39. An apparatus for determining the heart rate of a fetus, comprising:
 (a) means for obtaining a first signal indicative of fetal heart beats of a first fetus, said first signal derived from an ultrasound signal, and means for obtaining a second signal indicative of fetal heart beats of a second fetus and/or maternal heart beats;
 (b) first comparison means for comparing said first signal with said second signal and producing a third signal indicative of the coincidence between said first and second signals;
 (c) means for comparing said third signal to a limit;
 (d) means for generating a warning signal if said third signal bears a predefined relation to said limit; and
 (e) means for focusing said ultrasound signal in response to said warning signal.

40. An apparatus for determining the respective fetal heart rates of two fetuses, comprising:
 (a) means for obtaining a first signal indicative of fetal heart beats of a first fetus, said first signal derived from an ultrasound signal, and means for obtaining a second signal indicative of fetal heart beats of a second fetus and/or maternal heart beats of the mother of said first fetus;
 (b) means for processing one of said first and second signals with an adaptive filter with variable filter coefficients to obtain an output signal;
 (c) means for comparing said output signal with the other of said first and second signals and generating a difference signal based upon the comparison;
 (d) means for adapting said filter coefficients so that said difference signal is minimized;
 (e) means for generating a warning signal if a sum of one or more of said filter coefficients bears a predefined relation to a limit; and
 (f) means for focusing said ultrasound signal in response to said warning signal.

41. An apparatus for determining the respective fetal heart rates of two fetuses, comprising:
 (a) means for obtaining a first signal indicative of fetal heart beats of a first fetus, said first signal derived from an ultrasound signal, and means for obtaining a second signal indicative of fetal heart beats of a second fetus and/or maternal heart beats;
 (b) means for cross correlating said first and second signals with each other to produce a correlation function;
 (c) means for generating a warning signal if said correlation function exceeds a limit; and
 (d) means for focusing said ultrasound signal in response to said warning signal.

42. An apparatus for determining the heart rate of a fetus, comprising:
 (a) means for obtaining a first signal indicative of fetal heart beats of a first fetus and a second signal indicative of fetal heart beats of a second fetus and/or maternal heart beats;
 (b) first comparison means for comparing said first signal with said second signal and producing a third signal indicative of the coincidence between said first and second signals;
 (c) means for comparing said third signal to a limit;
 (d) means for generating a warning signal if said third signal bears a predefined relation to said limit; and
 e) means for obtaining an alternate signal indicative of heart beats of at least one of said first and second fetuses, and switching means for switching to a different combination of said first, second and alternate signals in response to said warning signal.

43. An apparatus for determining the respective fetal heart rates of two fetuses, comprising:
 (a) means for obtaining a first signal indicative of fetal heart beats of a first fetus and a second signal indicative of fetal heart beats of a second fetus;
 (b) means for processing one of said first and second signals with an adaptive filter with variable filter coefficients to obtain an output signal;
 (c) means for comparing said output signal with the other of said first and second signals and generating a difference signal based upon the comparison;
 (d) means for adapting said filter coefficients so that said difference signal is minimized;
 (e) means for generating a warning signal if a sum of one or more of said filter coefficients bears a predefined relation to a limit; and
 (f) means for obtaining an alternate signal indicative of heart beats of at least one of said first and second fetuses, and switching means for switching to a different combination of said first, second and alternate signal in response to said warning signal.

44. An apparatus for determining the respective fetal heart rates of two fetuses, comprising:
 (a) means for obtaining a first signal indicative of fetal heart beats of a first fetus and a second signal indicative of fetal heart beats of a second fetus;
 (b) means for cross correlating said first and second signals with each other to produce a correlation function;
 (c) means for generating a warning signal if said correlation function exceeds a limit; and
 (d) means for obtaining an alternate signal indicative of heart beats of at least one of said first and second fetuses, and switching means for switching to a different combination of said first, second and alternate signals in response to said warning signal.

45. An apparatus for determining the heart rate of a fetus, comprising:
 (a) means for obtaining a first signal indicative of fetal heart beats of a first fetus and a second signal indicative of fetal heart beats of a second fetus and/or maternal heart beats of the mother of said first fetus;
 (b) first comparison means for comparing said first signal with said second signal and producing a third signal indicative of the coincidence between said first and second signals;
 (c) means for comparing said third signal to a limit;
 (d) means for generating a warning signal if said third signal bears a predefined relation to said limit; and
 (e) hysteresis means for avoiding jitter in said warning signal.

46. An apparatus for determining the respective fetal heart rates of two fetuses, comprising:

(a) means for obtaining a first signal indicative of fetal heart beats of a first fetus and a second signal indicative of fetal heart beats of a second fetus;

(b) means for processing one of said first and second signals with an adaptive filter with variable filter coefficients to obtain an output signal;

(c) means for comparing said output signal with the other of said first and second signals and generating a difference signal based upon the comparison;

(d) means for adapting said filter coefficients so that said difference signal is minimized; and (e) means for generating a warning signal if a sum of one or more of said filter coefficients bears a predefined relation to a limit;

(f) hysteresis means for avoiding jitter in said warning signal.

47. An apparatus for determining the respective fetal heart rates of two fetuses, comprising:

(a) means for obtaining a first signal indicative of fetal heart beats of a first fetus and a second signal indicative of fetal heart beats of a second fetus;

(b) means for cross correlating said first and second signals with each other to produce a correlation function;

(c) means for generating a warning signal if said correlation function exceeds a limit; and (d) hysteresis means for avoiding jitter in said warning signal.

* * * * *

UNITED STATES PATENT AND TRADEMARK OFFICE
CERTIFICATE OF CORRECTION

PATENT NO. : 5,123,420

DATED : June 23, 1992

INVENTOR(S) : Guenter Paret

It is certified that error appears in the above-identified patent and that said Letters Patent is hereby corrected as shown below:

Column 12, line 8    change "hear" to -- heart --.

Column 13, line 27   change "if" to -- of --.

Column 6, line 59: should read as follows:

$$s = \text{signum}(d) = \begin{cases} -1 & \text{for } d < 0 \\ +1 & \text{for } d \geq 0 \end{cases} \qquad (1)$$

Column 7, line 5: should read as follows:

$$s = \text{signum}(d) = \begin{cases} -1 & \text{for } d \leq 0 \\ +1 & \text{for } d > 0 \end{cases} \qquad (2)$$

Signed and Sealed this

Twenty-ninth Day of March, 1994

Attest:

BRUCE LEHMAN

Attesting Officer    Commissioner of Patents and Trademarks